United States Patent [19]

Alexander

[11] Patent Number: 5,681,290

[45] Date of Patent: Oct. 28, 1997

[54] APPARATUS AND METHOD FOR PREVENTING TUG TRAUMA TO INTRAVENOUS OR INTRACAVITY INSERTION SITES

[75] Inventor: Gary E. Alexander, Baton Rouge, La.

[73] Assignee: Medisys Technologies, Inc., Baton Rouge, La.

[21] Appl. No.: 556,020

[22] Filed: Nov. 9, 1995

Related U.S. Application Data

[63] Continuation-in-part of Ser. No. 282,529, Jul. 28, 1994, Pat. No. 5,496,283.

[51] Int. Cl.$^6$ .................................................. A61M 5/32
[52] U.S. Cl. ............................................. 604/180; 604/174
[58] Field of Search ..................................... 604/174, 178, 604/179, 177, 180; 128/DIG. 26

[56] References Cited

U.S. PATENT DOCUMENTS

| | | | |
|---|---|---|---|
| 2,707,953 | 5/1955 | Ryan | 128/DIG. 26 X |
| 2,727,513 | 12/1955 | Muller | 128/DIG. 26 X |
| 3,630,195 | 12/1971 | Santomieri | 128/DIG. 26 |
| 3,834,380 | 9/1974 | Boyd | 128/DIG. 26 X |
| 4,224,937 | 9/1980 | Gordon | 128/DIG. 26 X |
| 4,480,639 | 11/1984 | Peterson et al. | 128/DIG. 26 X |
| 4,660,555 | 4/1987 | Payton | 128/DIG. 26 X |
| 4,985,019 | 1/1991 | Michelson | 128/DIG. 26 X |
| 5,112,312 | 5/1992 | Luther | 128/DIG. 26 X |
| 5,456,671 | 10/1995 | Bierman | 128/DIG. 26 X |
| 5,496,283 | 3/1996 | Alexander | 128/DIG. 26 X |

*Primary Examiner*—Sam Rimell
*Attorney, Agent, or Firm*—Roy, Kiesel & Tucker, PLC

[57] ABSTRACT

A tube securing device, and methods for using same, for preventing tug trauma to an intravenous or intracavity insertion site caused by movement of tubing is provided which comprises a flexible member, preferably disk-shaped, having a tube-securing structure affixed to one side and an adhesive applied to the opposite side wherein the tube-securing structure preferably extends from the perimeter area of the flexible member to the center area of the flexible member and is provided with parallel passageway and tube insertion slot extending throughout the length of the tube-securing structure sized to mechanically grip the tubing which is placed in the passageway to prevent its lateral movement in the passageway.

17 Claims, 4 Drawing Sheets

APPARATUS AND METHOD FOR PREVENTING TUG TRAUMA TO INTRAVENOUS OR INTRACAVITY INSERTION SITES

This is a continuation-in-part of U.S. patent application Ser. No. 08/282,529, now U.S. Pat. No. 5,496,283, filed on Jul. 28, 1994, which issued on Mar. 5, 1996.

BACKGROUND OF THE INVENTION

1. Field of the Invention

This invention relates to apparatus methods of eliminating trauma to a patient intravenous or catheter therapy site caused by unintentional pulling on the tubing extending between the intravenous needle or catheter and the fluid bag.

2. Prior Art

As part of treatment provided to a patient, fluids containing antibiotics or other type drugs may need to be introduced into the body or, in other cases, infectious body fluids drained from the body. One of the most common methods to introduce fluids into the body utilizes a system generally comprising an intravenous needle assembly connected to a fluid-containing bag by a length of plastic tubing. Such systems also generally have a clamping or valve means to control the rate of fluid flow from the bag and through the tubing to the needle. If fluids are being taken from the body, such systems generally comprise a catheter tube assembly connected to a fluid storage bag by a length of similar plastic tubing.

The needle or catheter tube, as the case may be, is inserted into the body at the appropriate site, referred to herein as the insertion site. In many cases, the intravenous needle or catheter may be required to be positionally fixed in the insertion site for long periods of time. It is therefore necessary to fix the needle assembly or catheter tube assembly so that the needle or catheter tube will remain in a fixed position while they are inserted into the insertion site. This is commonly done by taping the needle assembly or catheter tube assembly with adhesive tape at the insertion site.

Other devices and methods used for this purpose would include a suprapubic drainage system offered by Dow Corning under the brand name SILASTIC® CYSTOPATH. This system is used to fix a catheter tube at the insertion site which contains as one of its elements a circular disc having a catheter retention member extending across at least a portion of the disc diameter and provided with an opening in the member extending vertically through the disc directly above the insertion site for receiving the catheter tube. More particularly, an adhesive is first applied to the suprapubic area, and then applied to the bottom surface of the disc. The disc is then positioned on suprapubic area with the adhesive surface in contact and the center hole in the disc being placed over the catheter insertion site. The groove formed in the catheter retention member is aligned perpendicular to the midline of the patient. The needle is then inserted through the center hole and the anterior abdominal wall and into the bladder. The needle is withdrawn leaving the catheter in place. The catheter is then placed in the groove which will hold the catheter in a fixed position. Finally, in order to secure the disc from movement caused by tug trauma, tape is applied to the disc itself, to the catheter section extending from the disc, and to the tubing connecting the catheter to the drainage bag. This system is also described in U.S. Pat. 3,568,679 issued to Reif on Mar. 9, 1971.

Other devices designed to fix and hold a catheter or intravenous needle in a stable position as illustrated in U.S. Pat. No. 4,698,057 issued to Joishy on Oct. 6, 1987 (utilized suction cups affixed to winged structure to hold roller of adhesive tape that can more easily be dispensed to stabilize the catheter or I.V. needle in position), and U.S. Pat. No. 4,669,616 issued to Nowak on Oct. 13, 1987 (utilized a ratchetable clamp affixed vertically above a platform adhesively securable directly over the insertion site to secure the catheter in position).

Because the length of the tubing connecting the needle assembly or catheter tube assembly to the fluid bag must be of sufficient length to allow for some movement of the patient's body or the stand to which the fluid bag is attached, there is a great risk that the tubing may get hung up on bed rails when the patient moves or may be accidently pulled by a nurse or other person that is moving about the patient's bed. This tug force can be magnitudes greater than the ability of the insertion site tape or other insertion site fixing means to absorb without moving or dislodging the needle or the catheter tube. The movement or dislodgement of the catheter or intravenous tubing often leads to patient discomfort, fluid flow blockage, injury or perforation of the vein wall (the lumens), site irritation and inflammation with sepsis, and infiltration of the introduced fluid into surrounding muscular tissue. In the case of an intracavity drainage catheter, such movement or dislodgement can cause fluid flow blockage, internal and site sepsis, and patient discomfort. In each case, if the site is not adequately protected from such tugging, serious medical complications can result.

At present, the most commonly used method of attempting to prevent these difficulties is to use adhesive tape to separately fix the tubing to a patient's body. This additional taping is normally positioned far enough away from the insertion site so that the two tapings do not interfere with one another, yet close enough so as not to allow a long length of tubing to extend from the insertion site to the second taping position. Typically, the second taping is done a few inches away from the insertion site. In some cases the tubing is taped to the body in more than one place.

With time and repeated patient movement, tugs on the tubing frequently cause the tape to lose its adhesive grip on the tubing, even though it may retain its grip on the patient's skin. This permits the tugging, in increasing degrees as the tape fails to grip the tubing, to be transmitted to the needle assembly or catheter assembly with resultant hazardous and unsafe conditions described above.

This method of securing the tubing to the patient is not only time consuming, but does not allow for easy changing of the tubing or needle or catheter assembly without possible irritation to the patient's skin as the adhesive tape is removed.

To overcome the problems associated with tug trauma associated with jerking or pulling on the tubing extending from the catheter or intravenous needle, many different prior art devices have been developed. These are illustrated in U.S. Pat. No. 3,630,195 issued to Santomieri on Dec. 28, 1971 (tube receiving structure carried on an adhesive strip that provides for the tubing to be looped and mechanically fixed at two separate sections within the structure); U.S. Pat. No. 3,782,388 issued to Page on Jan. 1, 1974 (tube holding clip secured to an adhesive strip by a flexible, stretchable band); U.S. Pat. No. 4,170,995 issued to Levine on Oct. 16, 1979 (a tube clamp mounted on a post extending vertically from an adhesive base); U.S. Pat. No. 4,453,933 issued to Speaker on Jun. 12, 1984 (tube securing device affixed to a strap that can be fitted about the patient's wrist); and European Patent Application 247590 filed by Terumo Corporation on May 29, 1986 (circular tube having passageway to hold tubing).

Other prior art devices have been structured to both fix the catheter/intravenous needle, as well as secure the extending tubing to reduce tug trauma to the insertion site. Examples of these prior art devices include U.S. Pat. No. 3,834,380 issued to Boyd on Sep. 10, 1974 (a tube receiving cylinders affixed to an adhesive strip, at least one of which has a securing strap to cause the cylinder to mechanically grip the tubing), U.S. Pat. No. 4,419,094 issued to Patel on Dec. 6, 1983 (a catheter stabilizer designed to permit the catheter tubes to be snapped into a slit and then be inserted through an opening in a collar extending vertically over the insertion site); U.S. Pat. No. 4,711,636 issued to Bierman on Dec. 8, 1987 (an anchoring pad adhesively fixed to the patient and having separated bridge and tube securing cylinder for fixing a catheter and extending looped tubing, respectively, to the pad); U.S. Pat. No. 4,898,587 issued to Mera on Feb. 6, 1990 (a base plate adhesively affixed to the patient to which a catheter and the extending tubing are fixed by straps and then covered; U.S. Pat. No. 4,966,590 issued to Kalt on Oct. 30, 1990 (a base plate adhesively affixed to the patient having a flap to fix the intravenous needle and extended looped tubing to the base plate); and U.S. Pat. No. 5,147,320 issued to Reynolds et al on Sep. 15, 1992 (an anchoring pad adhesively affixed to the patient having a channel cut into the pad with barbs extending into the channel to fix a catheter and its extending tubing to the anchoring pad).

However, none of the above devices combines the criteria of manufacturing cost effectiveness, universality of uses, ease of application, permitting changing of tubing or needle/catheter assembly, adhesive permanence, reduced skin irritation, reduced crimping of the tubing, and force absorption capability desired by the medical community.

SUMMARY OF THE INVENTION

Objects and Advantages of the Invention

Therefore, it is an object of this invention to provide a tube securing device and a method of its use for reducing the possibility of tug trauma to the insertion site, which more closely meets the criteria desired by the medical community.

Another object of the invention is to provide a tube securing device that can be easily mass produced at cost effective prices.

Still another object of the invention is to provide a tube securing device that permits the tubing to be easily and quickly attached or removed from the device by medical personnel.

A further object of the invention is to provide a tube securing device that is sized and shaped with sufficient flexibility to permit its application on most parts of a patient's body.

A still further object of the invention is to provide a tube securing device that will adhere to a patient's skin for days without causing minimum skin irritation and without loss of adhesion.

Another object of the invention is to provide a tube securing device that will permit observation of the patient's skin to which the device has been adhered to permit detection of any skin irritation.

A further object of the invention is to provide a tube securing device that can absorb most of the tug trauma common in intravenous or intracavity situations to prevent damage to the insertion site by movement of the intravenous needle or catheter tube.

Still another object of this invention is to provide a tube securing device which requires little additional training of the medical personnel involved with its application and use.

Other advantages and objects of this invention will become apparent from the ensuing descriptions of the invention.

Statement of the Invention

Accordingly, a tube securing device for preventing tug trauma to an intravenous or intracavity insertion site caused by movement of tubing is provided which comprises a flexible member, preferably disk-shaped, having a tube-securing structure affixed to one side and an adhesive applied to the opposite side. The tube-securing structure preferably extends from a section of the perimeter area of the flexible member to the center area of the flexible member. The tube-securing structure is shaped to form a passageway parallel to a tube insertion slot, both of which extend throughout the length of the tube-securing structure. The passageway and tube insertion slot both being sized to cause the tube-securing structure to mechanically grip the tubing placed in the passageway so as to prevent its lateral movement in the passageway.

In use, a section of tubing having an intravenous needle or catheter affixed at one end and a fluid-containing bag or fluid receiving bag affixed at its opposite end is positioned in the tube-securing structure passageway whereby the intravenous needle or catheter is attached at that end of the tubing which extends a desired distance from the end of the passageway positioned at a section of the perimeter area of the flexible member and whereby the bag is attached at the opposite end of the tubing which extends from the center area of the flexible member. The flexible member is secured to the patient's body at the tubing securing site which is located at some desired distance from the insertion site. The flexible member may be secured to the patient's body prior to securing the tubing in the tube retaining structure passageway, but preferably after the tubing has been secured in the passageway.

DESCRIPTION OF THE PREFERRED EMBODIMENTS

Figure 1A:
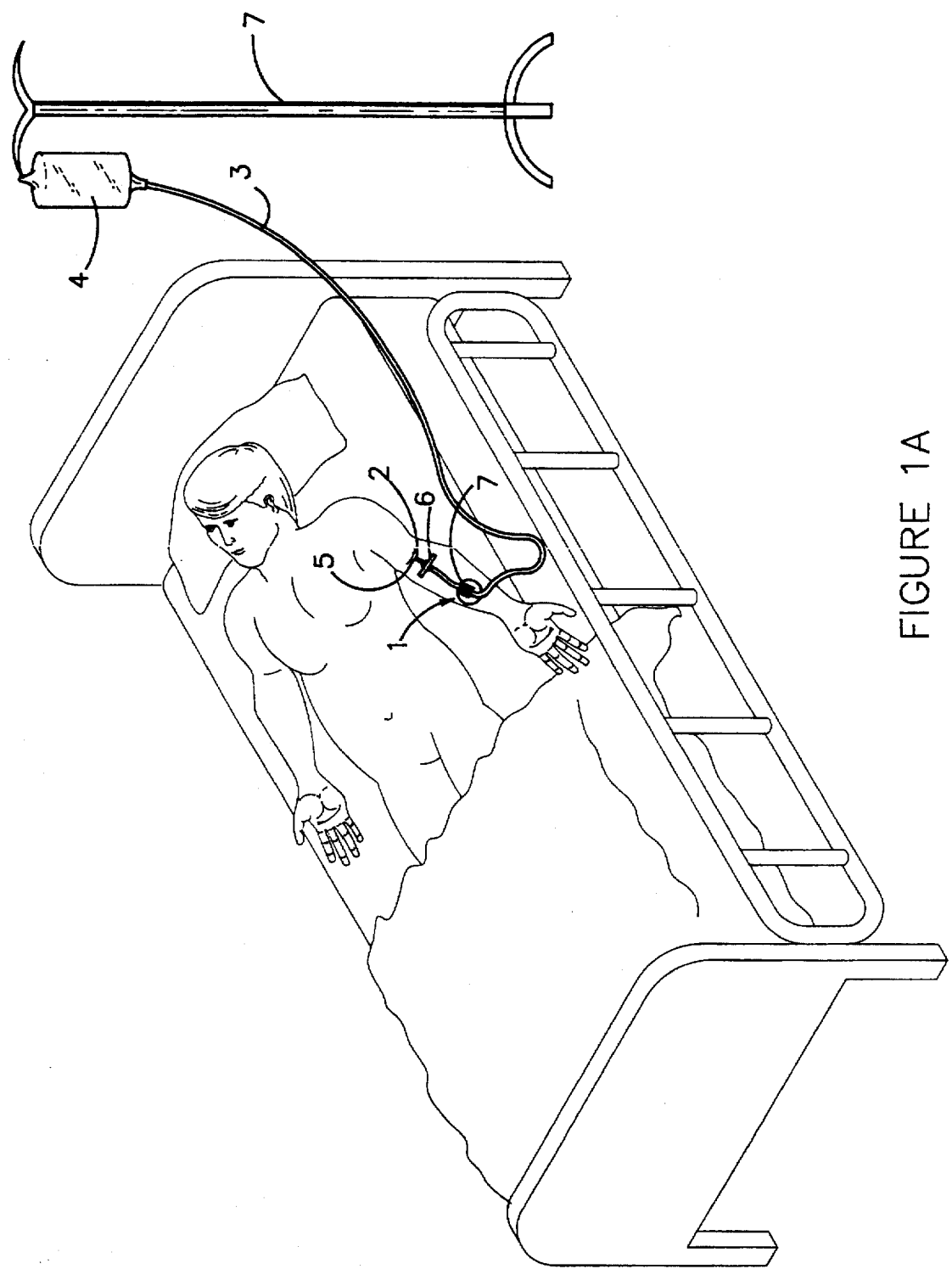
FIG. 1A is a perspective view of a preferred embodiment of the tug trauma reducing device utilized with an intravenous needle assembly.

FIG. 1A depicts a conventional arrangement when a preferred embodiment of the tug trauma reducing member 1 is used in conjunction with an intravenous fluid injection procedure. In this arrangement, the needle assembly having intravenous needle 2 is fluidly connected by means of plastic tubing 3 to a fluid source, such as fluid containing bag 4. The needle 2 is inserted into a patient's arm at the insertion site 5 and held in position by a holding device 6 such as shown in U.S. Pat. No. 4,834,380. It is also typical for a movable stand 7 to be provided near the patient's bed to position fluid containing bag 4 at a height above insertion site 5 to facilitate the flow of fluids from fluid containing bag 4 to needle 2 and then into the patient's vein.

Figure 1B:
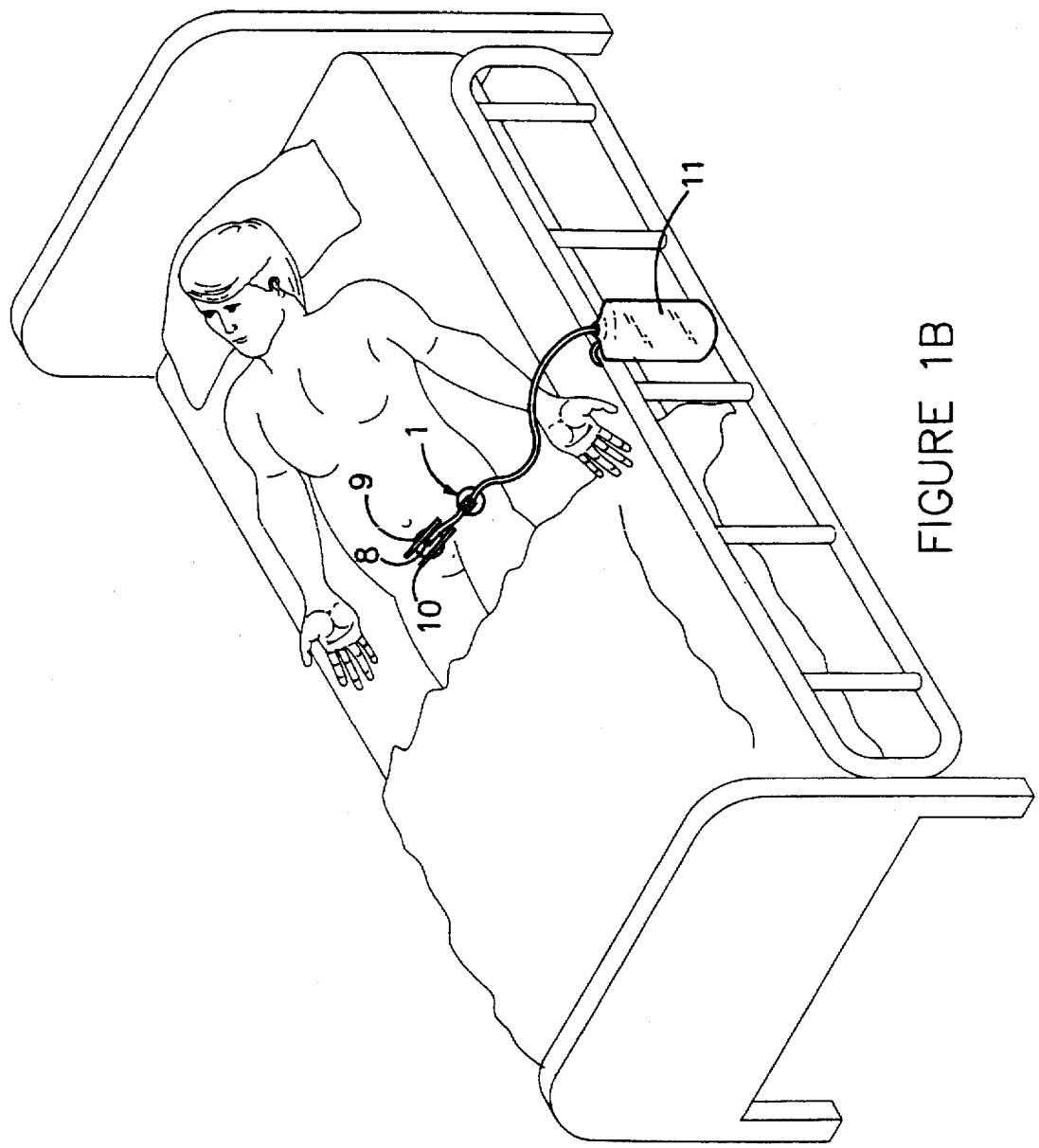
FIG. 1B is a perspective view of a preferred embodiment of the tug trauma reducing device utilized with a catheter assembly.
Figure 2:
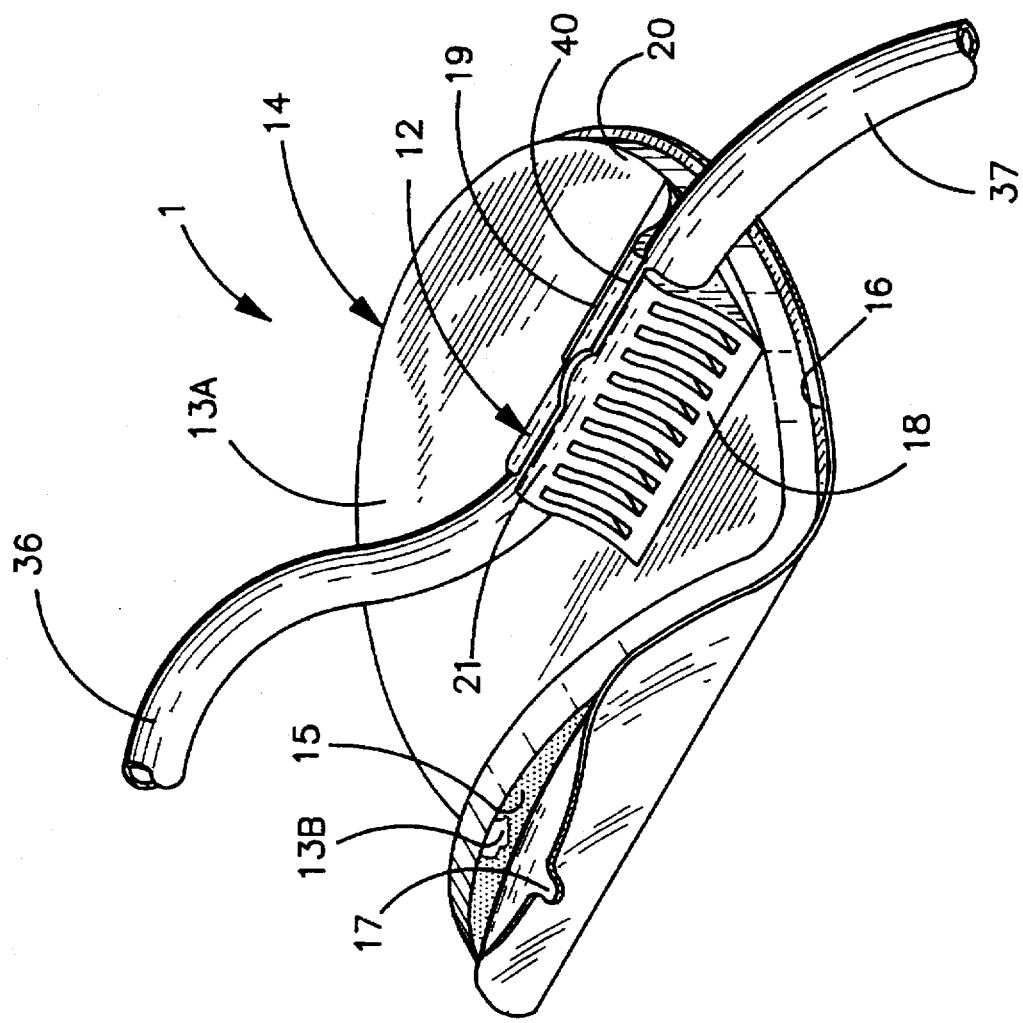
FIG. 2 is a perspective view of another preferred embodiment of the invention which may be used with either an intravenous needle assembly or a catheter assembly wherein the body has been turned up and the adhesive covering partially pulled away and a section of the adhesive removed to illustrate the bottom surface of the insertion body.

In FIG. 1B the tug trauma reducing member 1 is used in conjunction with an intracavity catheter assembly to remove fluids from the patient. In this arrangement the catheter 8 is held in position above the insertion site 5 by a holding device 9, such as a SILASTIC® Cystopath Body Seal further fixed to the patient's body by tape strips 10. The tug trauma reducing member 1 having the tubing 4 mechanically locked thereto is positioned a short distance from the holding device 9. A drainage bag 11 is affixed to the bed railing by conventional clip means at a position below the insertion site 5 to facilitate the flow of infectious body fluids from catheter 8 through tubing 3 and into drainage bag 11.

Referring to FIGS. 2, 3A and 3B, and 4 tug trauma reducing member 1 is formed having an elongated, tube-securing structure 12 formed on a first side 13A of a relatively thin, flexible body 14 An adhesive composition 15 is applied on the opposite side 13B of body 14 and prevented from sticking to an undesired surface by a conventional throw-away covering 16 that is removed before member 1 is ready to be attached to the patient. Covering 16 is removed from the adhesive 15 by pulling on tab 17.

Figure 5:
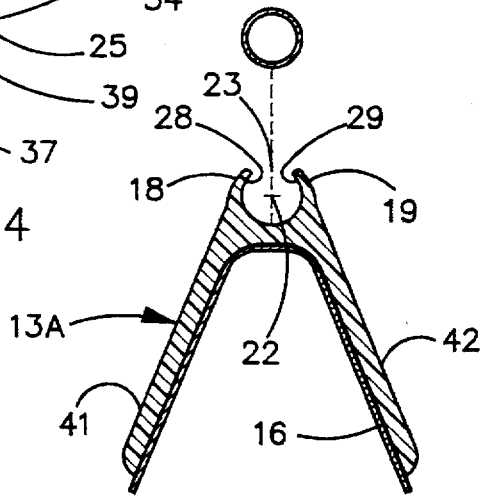
FIG. 5 is an end view illustrating the opening of the lateral tubing slot that permits the tubing to be easily inserted into the passageway formed by the opposing wall surfaces of the shoulder members.
Figure 3A:
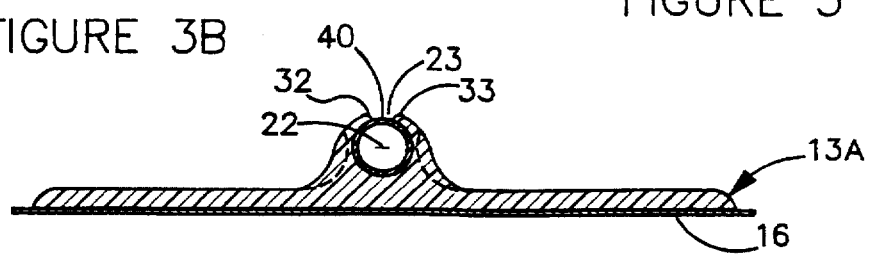
FIG. 3A is a cross-sectional view of the invention taken along line 3A—3A of FIG. 4 that illustrates the mechanical gripping of the tubing by the shoulder member wall surfaces forming a passageway and a lateral tubing slot extending between the shoulder members.

It is preferred that tube-securing structure 12 and body 11 be formed from the same pliable plastic or rubber material which will readily conform to the shape of the arm or other body member to which it will be secured. This preferred construction will also permit both pieces to be more easily molded as a unitary piece. More preferably, tube-securing structure 12 will be constructed from material which is sufficiently clear to allow a nurse or treating physician to determine if any rash develops on the patient's skin under the tube-securing structure 12. Structure 12 is preferably constructed of two parallel shoulder members 18 and 19 that extend laterally along first side 13A from a perimeter area 20 to the center area 21 of body 14. Shoulder members 18 and 19 are separated from one another to form passageway 22 and lateral slot 23 that extend from the perimeter area ends 24, 25 of shoulder members 18, 19, respectively, to the center area end 26, 27 of shoulder members 18, 19, respectively. Passageway 22 is sized to be slightly smaller than the external diameter of tubing 3 so that when shoulder member wall surfaces 28, 29 that form passageway 22 contact tubing 3, they will mechanically grip tubing 3 to prevent it from lateral movement in passageway 22. Lateral slot 23 is sized so that its width is less than the external diameter of tubing 3, but as shown in FIG. 5, wide enough when spread open by pulling down on opposite surface section 11, 12 of side 13A to permit tubing 3 to be positioned in passageway 22.

In a more preferred embodiment, shoulder members 18, 19 will each be constructed to form cooling fins 30, 31, respectively, that permit the more rapid molding of member 1, as well as permits the utilization of less material to form member 1. Such construction also permits, for the particular material used, construction of a tube-securing structure 12 having greater flexibility in expanding the width of lateral slot 23 when inserting tubing 3 into passageway 22.

In a preferred embodiment the width of each fin 30, 31 will be approximately 3/16 to 1/4 of an inch and will be separated from each other by approximately the same distance. Each fin 30, 31 will extend outward from first side 13 to the slot forming lip area 32, 33 of shoulder member 18, 19, respectively.

In another preferred embodiment body 14 and shoulder members 18, 19 will be molded from at least 50, and more preferably about 80 durometer polyurethane material, such as Dow 2363-80A manufactured by Dow Chemical Company. It has been found that this material provides the preferred amount of flexibility and resiliency, as well as the desired aging characteristics. In addition, this material provides the preferred amount of molecular bonding to the tubing 3 in passageway 22 to better ensure the reduction of tug trauma to the insertion site 5.

As indicated above, tube-securing structure 12 extends from a section of the perimeter area 20 to the center area 21 of first side 13. This preferred configuration maximizes both the mechanical gripping surface on tubing 3 when it is placed within passageway 22, as well as the amount of tubing tug force that member 1 can absorb before becoming detached from the patient.

It is preferred that substantially all sections of the wall surfaces 28, 29 forming passageway 22 contact tubing 3 when tubing 3 is placed in passageway 22 so as to increase the molecular bonding or total coefficient of friction forces between the wall surfaces, 28, 29 and tubing 3.

In another alternate embodiment, wall surfaces 28, 29 form a section 34 of passageway 22 whose centerline is arcuate in shape. Although it may be more difficult to insert tubing 3 into passageway 22 with this shape, greater gripping force can be provided to tubing 3 by wall surfaces 28, 29 to prevent tubing 3 from being moved once it is positioned in passageway 22.

It is preferred that the adhesive applied to the second or opposite side 13B of member 1 be Dow Avery-Dennison Med 6309, or a similar adhesive that will harden on exposure to air and will maintain its adhesive ability for up to five days. In addition, the adhesive should not become an irritant to the patient's skin during this period of time. Furthermore, the adhesive should be such to permit removal of the member 1 with minimum, or no damage to patient's skin. The adhesive is prevented from hardening until the member 1 is ready to be applied to the patient by a conventional paper or plastic throw-away covering 16 having tab 17 to assist in removing the covering 16.

Figure 4:
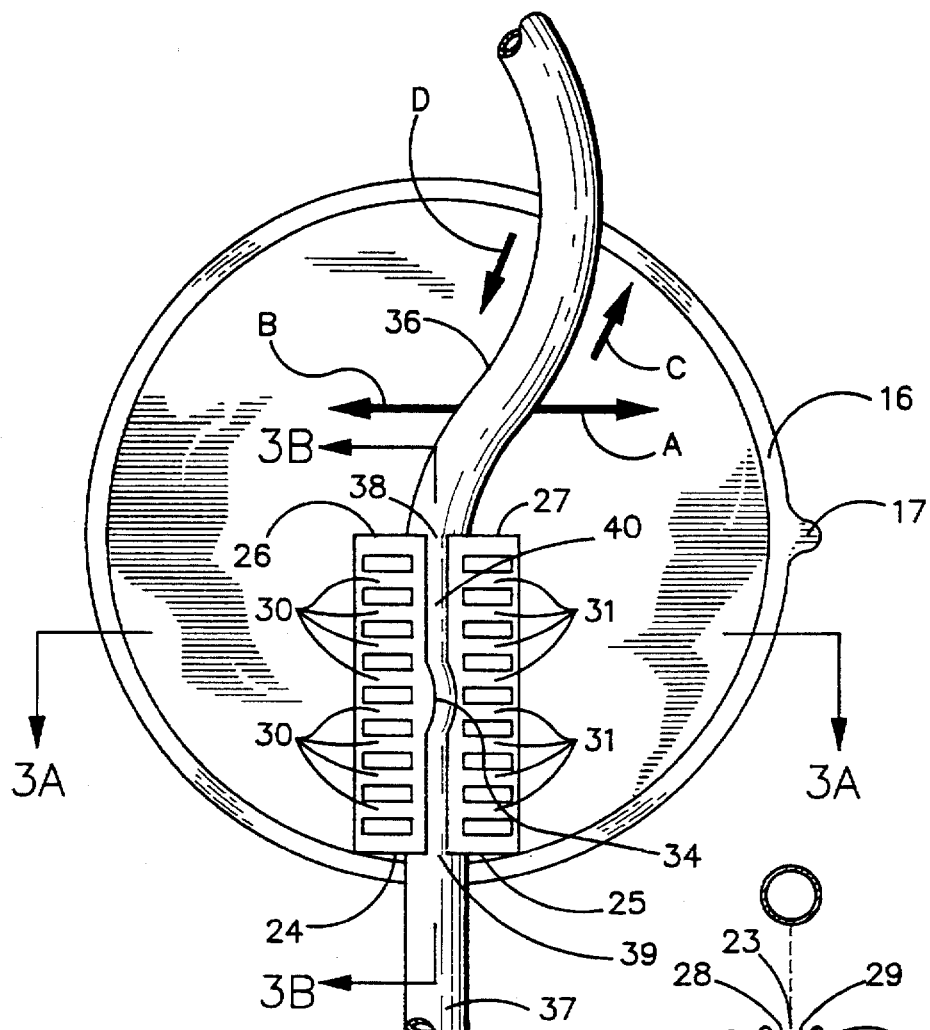
FIG. 4 is a top view of the invention illustrating some of the various movement of the tubing associated with tug trauma.
Figure 3B:
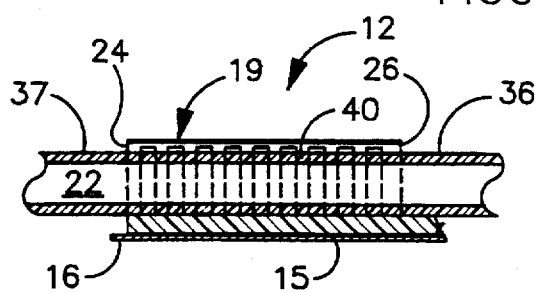
FIG. 3B is a cross-sectional view of the invention taken along line 3B—3B of FIG. 4 that illustrates the preferred shoulder member wall construction.

Referring to FIG. 4, it is seen that member 1 offers significant advantages over conventional taping and other methods for securing catheters, intracavity medical tubing, or other similar devices. The most common tug trauma results from sudden jerks or pulls on section 36 of tubing 3 that extends from center area ends 26, 27 to the fluid-containing bag 4 or the drainage bag 11. This tug trauma can be caused any number of ways. The most common ways result from the patient moving his arms or rolling over on tubing section 36, or from an attending person accidently pulling on tubing section 36 when moving about the patient or moving stand 3. This can cause substantial torquing or twisting forces to be placed at the center area ends 26, 27.

To insure that these forces do not cause tug trauma at the insertion site 5, it is common to apply substantial tape about tubing 3 in order to secure it to the patient's body. However, as shown in FIG. 5, when utilizing member 1, tubing section 40 is fixed within passageway 22 by bending the edges 41, 42 of body 14 toward one another so as to force open lateral slot 23 to permit tubing section 40 to be positioned in passageway 22. Once tubing section 40 is positioned in passageway 22, then the edges 41, 42 of body 14 are allowed to return by the natural resiliency of body 14 to their normal position which closes lateral slot 23 and forces wall surfaces 28, 29 against tubing 3 to mechanically lock tubing section 40 in passageway 22. In the method of this invention, tubing 3 is positioned in passageway 22 so that end of tubing 3 connected to bag 4 or 11, as the case may be, exits from passageway 22 at the center area 21. In a more preferred method, tubing 3 is positioned in passageway 22 to minimize the slack in tubing 3 between perimeter area 20 and the insertion site 5 to reduce the risk of tug trauma to the insertion site 5 caused by tugging on section 37 of tubing 3 extending between perimeter area ends 24, 25 and needle 2 or catheter 8, as the case may be.

Because entry opening 38 into passageway 22 is located at the center area 21, any forces applied to tubing 3 as shown by the directional arrows A–D are substantially less likely to pull member 1 from the patient's skin because there is more adhesive surface that must be lifted, than if entry opening 38 were located near the perimeter area 20 of member 1.

Directional arrow A represents lateral movement of tubing section 36 in a clockwise rotation caused by some force. This force can be, for instance, movement of tubing section 36 by medical personnel. Tubing section 36 will move until it pivots about entry opening 38. This pivoting movement transfers the forces to center area ends 26, 27 of shoulder members 18, 19, respectively. If a substantial force is applied to tubing 3 in a clockwise direction, any further movement will be absorbed by center area ends 26, 27, and continued application of force will then be transferred to shoulder members 18, 19, respectively. If the force is great enough, then the shoulder members 18, 19 may cause body 14 to rotate slightly on the patient's skin. However, the adhesive side 13 being attached to the patient's skin causes the rotation to be about the center area 21 of body 14.

Likewise, if tubing section 36 is moved in a counter-clockwise direction as illustrated by directional arrow B, then the forces will again be transferred to center ends 26, 27. It is noted that the rotation resulting from these forces will cause some rotational movement to body 14. For this reason, it is preferred in that section 37 of tubing 3 extending from exit opening 39 at the perimeter area 20 to the insertion site 5 be provided with some slack to compensate for the rotational movement to prevent any tug trauma at the insertion site 6.

Directional arrow C depicts movement of tubing section 36 in the longitudinal direction, such as may be caused by a pulling on tubing 3. In this case, the elasticity forces of shoulder members 18, 19 causing lip areas 32, 33 to return to their normal position, as well as frictional or molecular bonding forces between shoulder member wall surfaces 28, 29 against tubing section 40 absorb these longitudinal forces preventing tubing section 40 from being pulled out of passageway 22. In still another embodiment, passageway 22 may have a cross-section of varying diameters wherein at least one of the cross-sectional areas is less than the cross-sectional area of tubing section 40.

If tubing section 36 is subjected to a compressional force as illustrated by directional arrow D, then most of the compressional force should also be similarly absorbed.

Although it is preferred that body 14 be generally circular in shape when viewed from above, body 14 can still perform its function if it is rectangular, oblong, triangular or some other shape which permits sufficient adhesive surface to exist from center area 21 to the perimeter area 20 to prevent member 1 from being pulled off of the patient's body by normal tug trauma. A distance of about at least one inch from the center area 21 to the closest perimeter point has been found to provide sufficient adhesive surface when using the adhesives described herein.

In another alternate embodiment, adhesive may be applied to wall surfaces 28, 29 to ensure that tubing 3 is affixed in passageway 22. This adhesive may be the same as adhesive 15.

There are, of course, other obvious embodiments of the invention which are intended to be included within the scope of the claims set forth below.

What I claim is:

1. A device for preventing tug trauma to an intravenous or intracavity insertion site caused by movement of tubing extending from the insertion site to a fluid bag, which comprises:

(a) a flexible member having a first and second side separated by a perimeter edge, (b) adhesive applied to said first side, and (c) a tube-securing structure affixed to said second side and extending from said perimeter edge to a center area of said first side, wherein:

(i) said tube-securing structure comprises a first and second flexible shoulder member having facing wall surfaces forming a passageway and a tubing insertion slot parallel to one another that extend throughout the length of said tube-securing structure, and (ii) said passageway having a section for receiving and mechanically gripping of tubing positioned in said section of said passageway, and (iii) said tubing insertion slot having a width sufficient for permitting tubing to be positioned in said passageway when said first and second shoulder members are flexed away from each other, and sufficient for preventing tubing positioned in said passageway from passing through said tubing insertion slot when said first and second shoulder members are in their normal position, and wherein said flexible member and said tube-securing structure are unitarily formed from a polyurethane compound having a durometer hardness of greater than 50.

2. A device according to claim 1 wherein said compound is sufficiently transparent to permit viewing of the skin of said patient beneath said flexible member.

3. A device according to claim 1 wherein said durometer hardness is about 80.

4. A device according to claim 1 wherein said first shoulder member is shaped with a series of cooling fins extending outward therefrom.

5. A device according to claim 2 wherein said first shoulder member is shaped with a series of cooling fins extending outward therefrom.

6. A device according to claim 3 wherein said first shoulder member is shaped with a series of cooling fins extending outward therefrom.

7. A device according to claim 1 wherein each of said cooling fins is approximately $3/16$–$1/4$ inches wide and separated from any adjacent cooling fin by approximately $3/16$–$1/4$ inches.

8. A device according to claim 1 wherein said flexible member is disk-shaped.

9. A device according to claim 1 wherein said facing wall surfaces mechanically grip said tubing.

10. A device according to claim 5 wherein a substantial portion of said facing wall surfaces mechanically grip said tubing.

11. A device according to claim 1 wherein said first and second shoulder members form said passageway having an arcuate section.

12. A device according to claim 5 wherein said adhesive is applied to said facing wall surface.

13. A device according to claim 6 wherein said adhesive is applied to said facing wall surface.

14. A device according to claim 1 wherein said adhesive is applied to said facing wall surface.

15. A device according to claim 7 wherein said adhesive and said second adhesive are the same.

16. A device for preventing tug trauma to an intravenous or intracavity insertion site caused by movement of tubing extending from the insertion site to a fluid bag, which comprises:

(a) a flexible member having a first and second side separated by a perimeter edge, (b) adhesive applied to said first side, and (c) a tube-securing structure affixed to said second side and extending from said perimeter edge to a center area of said first side, wherein:

(i) said tube-securing structure comprises a first and second flexible shoulder member having facing wall surfaces forming a passageway and a tubing insertion slot parallel to one another that extend throughout the length of said tube-securing structure, and (ii) said passageway having a section for receiving and mechanically gripping of tubing positioned in said section of said passageway, and (iii) said tubing insertion slot having a width sufficient for permitting tubing to be positioned in said passageway when said first and second shoulder members are flexed away from each other, and sufficient for preventing tubing positioned in said passageway from passing through said tubing insertion slot when said first and second shoulder members are in their normal position, and wherein said first shoulder member is shaped with a series of cooling fins extending outward therefrom.

17. A device for preventing tug trauma to an intravenous or intracavity insertion site caused by movement of tubing extending from the insertion site to a fluid bag, which comprises:

(a) a flexible member having a first and second side separated by a perimeter edge, (b) adhesive applied to said first side, and (c) a tube-securing structure affixed to said second side and extending from said perimeter edge to a center area of said first side, wherein:

(i) said tube-securing structure comprises a first and second flexible shoulder member having facing wall surfaces forming a passageway and a tubing insertion slot parallel to one another that extend throughout the length of said tube-securing structure, and (ii) said passageway having a section for receiving and mechanically gripping of tubing positioned in said section of said passageway, and (iii) said tubing insertion slot having a width sufficient for permitting tubing to be positioned in said passageway when said first and second shoulder members are flexed away from each other, and sufficient for preventing tubing positioned in said passageway from passing through said tubing insertion slot when said first and second shoulder members are in their normal position, and wherein a second adhesive is applied to said facing wall surface.

* * * * *